United States Patent [19]

Biedermann

[11] 4,058,571

[45] Nov. 15, 1977

[54] CONTINUOUS PROCESS FOR THE PRODUCTION OF D,L'MENTHOL

[75] Inventor: Wolfgang Biedermann, Krefeld-Bockum, Germany

[73] Assignee: Bayer Aktiengesellschaft, Leverkusen, Germany

[21] Appl. No.: 624,144

[22] Filed: Oct. 20, 1975

Related U.S. Application Data

[63] Continuation of Ser. No. 452,592, March 19, 1974, abandoned.

[30] Foreign Application Priority Data

Mar. 24, 1973 Germany .............................. 2314813

[51] Int. Cl.² .................... C07C 27/04; C07C 35/12
[52] U.S. Cl. ............................. 260/631 H; 252/471
[58] Field of Search ..................................... 260/631 H

[56] References Cited

U.S. PATENT DOCUMENTS

| | | |
|---|---|---|
| 2,843,636 | 7/1958 | Booth .............................. 260/631 H |
| 2,866,826 | 12/1958 | McLaughlin et al. .......... 260/631 H |
| 3,405,185 | 10/1968 | Houlihan et al. ................ 260/631 H |
| 3,558,703 | 1/1971 | Adam et al. ......................... 260/563 |

OTHER PUBLICATIONS

Leffingwell et al., Synthesis of L-menthol from a Citrus by-product, pp. 1–14, (1973).

*Primary Examiner*—James O. Thomas, Jr.
*Assistant Examiner*—James H. Reamer
*Attorney, Agent, or Firm*—Burgess, Dinklage & Sprung

[57] ABSTRACT

Continuous process for production of d,l, menthol by hydrogenation of thymol or other compound having the carbon skeleton of menthol and which is substituted by oxygen (oxygen or hydroxy) in the 4-position. A cobalt-manganese catalyst is used which contains 10 to 40% by weight of manganese based on the total quantity of oxidic cobalt and oxidic manganese. High conversion are obtained and the built up of by-products is low. The catalyst is similarly effective for rearrangement of isomers of menthol to product d,l-menthol.

14 Claims, No Drawings

CONTINUOUS PROCESS FOR THE PRODUCTION OF D,L'MENTHOL

This is a continuation, of application Ser. No. 452,592, filed Mar. 19, 1974 now abandoned.

BACKGROUND

This invention relates to a continuous process for the production of d,l-menthol, and to the catalyst used in this process.

As it is known d,l-menthol, in the form produces in the examples herof, is useful for example in perfumes.

It is known that d,l-methol can be obtained by the batch catalytic hydrogenation of thymol and other compounds which have the carbon skeleton of menthol with at least one double bond and which are substituted by oxygen in the 4-position. It is also possible to obtain d,l-menthol by racemising and/or rearranging d-menthol and the optically active or inactive stereoisomers of menthol, for example by heating these compounds with hydrogen in the presence of a hydrogenation catalyst. A crude product containing d,l-menthol d,l-neomenthol and d,l-isomenthol in a weight ratio of about 6 : 3 : 1, corresponding to a state of equilibrium, is generally obtained, irrespective of the particular starting material, both in the case of catalytic hydrogenation and in the case of racemisation on account of the epimerisation which takes place in both processes. In addition to the two aforementioned stereoisomers, however, secondary products such as d,l-neoisomenthol, menthone and the stereoisomeric ketones, d,l-neomenthone and d,l-isomenthone are also formed together with menthenone and hydrocarbons (menthenes and menthane). The fact that it is difficult if not impossible to reduce the formation of these secondary products and/or to rearrange them into d,l-menthol, accounts for the considerable disadvantages of conventional processes. In the process according to U.S. Pat. Specification No. 2,843,636 for example, nonreuseable hydrocarbons are formed in a quantity of about 5%, whereas, as our own tests have shown, approximately 7% of undesirable secondary products are formed in the process according to U.S. Pat. Specification No. 2,871,272 which does not give any analytical data in respect of the resulting crude product.

These disadvantages become particularly noticeable when attempts are made to carry out the processes, described only in their batch form, in a continuous cycle by separating the d,l-menthol from the product stream by physical processes and recycling the secondary products. These undesirable secondary products accumulate so quickly in the recycle stream that continuous working becomes uneconomical.

THE INVENTION

We have now found that d,l-menthol can be obtained by catalytically hydrogenating compounds which have the carbon skeleton of menthol with at least one double bond and which are substituted by oxygen in the 4-position, and/or by rearranging optically active or inactive stereoisomers of menthol at elevated temperature and under pressure, provided that hydrogenation is carried out continuously using a fixed-bed, cobalt catalyst containing 10 to 40% by weight of manganese, based on the total quantity of cobalt and manganese, the quantity of hydrogen per mol preferably amounts to at least 10 times the quantity required to hydrogenate a benzene nucleus, at a temperature in the range from 170° to 220° C and under a pressure of at least 25 bars.

Thus, the invention provides a process for the production of d,l-menthol, which comprises continuously introducing into a contacting zone containing a catalyst for the reaction, an admixture of hydrogen and starting material for contacting of the hydrogen and starting material with the catalyst for reaction of the hydrogen and starting material to form the d,l-menthol, and maintaining the temperature and pressure and residence time in the contacting zone sufficient for the reaction, and continuously withdrawing the d,l-menthol from the contacting zone.

The catalyst is a cobalt-manganese catalyst containing 10 to 40% by weight of manganese, based on the total quantity of oxidic cobalt and oxidic manganese. Preferably, the catalyst is the product of precipitating the hydroxides or carbonates of cobalt and manganese, calcining the precipitate to produce oxide of the cobalt and manganese, and reducing the oxide with hydrogen, and the reduced catalyst, when analyzed by X-ray photography in the absence of air does not show any reflexes attributable to the presence of crystalline cobalt or crystalline manganese compounds.

The catalyst is a reduced cobalt-manganese oxide effective to catalyze hydrogenation of the starting material to d,l-menthol.

The starting material is a compound having the carbon skeleton of menthol and is convertible to d,l-menthol by catalytic hydrogenation, and has at least one double bond and is substituted in the 4-position by oxygen. Preferably, the starting material is of the formula:

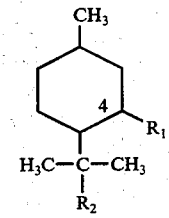

wherein:
R₁ is oxygen or hydroxy
R₂ is hydrogen
R₂ is nothing,
there is at least one double bond in the compound.

The amount of hydrogen is, preferably, at least 10 times the amount required to hydrogenate the benzene nucleas, i.e., at least 10 times the amount required (i.e., utilized) to fully hydrogenate X moles of benzene, wherein X is the number of moles of starting material. Because the process of invention is carried out in the presence of hydrogen, secundary dehydrogenation reactions are reduced.

The process of the invention can also be used for production of d,l-menthol by rearranging optically active or inactive isomers of menthol to form d,l-menthol. The isomer can be at least one of d-menthol, l-menthol, d-neomenthol, l-neomenthol, d-isomenthol, l-isomenthol, d,l-neomenthol, d,l-isomenthol.

It is preferred to use a cobalt catalyst containing from 15 to 30% by weight and more particularly from 20 to 25% by weight of manganese. This catalyst may optionally be activated with small quantities of copper of up to 1% by weight, preferably from 0.05 to 0.5% by weight, based on the total weight of the catalyst. In this way, it is possible where necessary to work at somewhat lower temperatures under otherwise the same reaction conditions. Similarly, it is also possible where necessary even further to reduce the formation of high-boiling secondary products such as dimenthones which, in cases where a non-activated catalyst is used, generally make up less than 0.05% by weight of the reaction product.

The process works with a fixed-bed catalyst in the gas or trickle phase. The process according to the invention is preferably carried out with an excess of hydrogen of about 20 times the quantity required to hydrogenate a benzene nucleus. The preferred temperature range is from 180° C to 210° C. The process is preferably carried out under a pressure of higher than 100 bars and more particularly under a pressure of higher than 200 bars. The upper limit to the pressure applied is determined both by technical and by economic considerations. Under the reaction conditions applied, the hydrogenation, racemisation and isomerisation stages of the process according to the invention surprisingly take place so mildly that the formation of unuseable secondary products (hydrocarbons) is reduced by around 90% and the formation of undesirable secondary products by around 70% in relation to conventional processes.

The fact that the process according to the invention can be successfully carried out must be regarded as extremely surprising. Although nickel catalysts and nickel-copper catalysts activated with small quantities of manganese of up to about 5%, preferably with 0.3 to 0.7% of manganese, have already been proposed for the production of saturated, cycloaliphatic alcohols from phenols (cf. German Auslegeschrift No. 1,090,200), this addition simultaneously promotes formation of the corresponding ketone (cf. German Patent Specification No. 383,540). Thus, our own tests have shown that pure activation of the cobalt catalyst, as known from German Auslegeschrift No. 1,090,200, does not produce any better results than a non-activated catalyst.

By contrast, it is possible with the catalyst used in the process according to this invention to obtain not only outstanding results in the hydrogenation of phenols, but also excellent yields in the catalytic hydrogenation of compounds which have the carbon skeleton of menthol with at least one double bond and which are substituted by oxygen in the 4-position, to form d,l-menthol, and in the racemisation and/or rearrangement of d-menthol and the optically active or inactive stereoisomers of menthol.

The starting materials used for the process according to the invention are known (Ullmanns Enzoklypadie der techn. Chemie, 3rd Ed., Munich 1966, Vol. 17, pages 24, 25, U.S. Patent Specification No. 2,843,636). The following are mentioned by way of Example: thymol, menthone, 1-p-menthan-3-one of Merck Index, 8th Ed., p. 654, menthenone, piperitone; pulegone of Merck Index, 8th Ed. p. 838, 886, d-and l-menthol, d-and l-neomenthol, d-and l-isomenthol, d,l-neomenthol, d,l-isomenthol. These compounds can be used both individually and in admixture with one another.

The production of manganese-containing cobalt catalysts which can be used for the process according to the invention is also known and can be carried out by conventional methods cf. Catalysis Vol. I, pages 315 – 352, New York, 1954 (Library of Congress Catalogue Card No. 54-6801); Dolgow, Die Katalyse in der organisch chem Chemie, pages 38 – 45, VEB Deutscher Verlag der Wissenschaft, Berlin 1963; German Patent Specification No. 1,568,188).

In general, the catalysts are prepared by precipitating the hydroxides or carbonates from aqueous solutions of corresponding metal salts, followed by filtration, drying and, optionally, calcination or decarbonisation, i.e. conversion into oxidic form.

If the resulting catalysts accumulate in powder form, they can be prepared in known manner by compressing the catalyst powder following the addition of, for example, 1 to 2% by weight of graphite as lubricant, breaking up the resulting compressed powder and recompressing it, i.e. with preconsolidation.

The catalysts thus obtained are subsequently converted into the active form by reduction with hydrogen.

It can be particularly advantageous to reduce the catalysts with hydrogen before they are used to such an extent that, from the form $Co_2MnO_4$ which can only be detected by X-ray photography in the non-reduced catalyst, the catalyst is obtained in the CoO-form which, on analysis by X-ray photography, does not show any reflexes attributable to the presence of crystalline cobalt or crystalline manganese compounds.

It can be of particular advantage directly to use the catalysts obtained in active form. Accordingly, it is advantageous to reduce the catalyst in the process apparatus itself. After the active form of the catalyst has been obtained by reduction with hydrogen, the reaction conditions are adjusted in regard to temperature and pressure, input of the starting material is commenced and the process according to the invention is carried out.

It can be advantageous to carry out the process according to the invention in tubular reactors comprising one or more tubes and to pass the starting materials over the catalyst fixedly arranged in the reaction tubes. For example, the reaction tubes can have lengths of from 2 to 20 meters and internal diameters of 20 to 800 mm. The catalysts can have a grain size of, for example, 3 to 8 mm. The apparatus required for the process according to the invention, and the method by which the process is carried out, are well known in the art.

However, the process according to the invention is advantageously carried out as follows:

The excess hydrogen which is not consumed during the reaction is recycled. The mixture of starting materials, which is liquid or solid according to its composition, is if necessary, liquefied by heating and suitably introduced into the hydrogen circuit, for example by means of an injection pump. The stream of hydrogen laden with the starting material is heated in a heat exchanger by the hot countercurrent output stream coming from the reactor, subsequently brought to the reaction temperature in a preheater and introduced into the reactor. The temperature of the reactor is kept substantially constant at the reaction temperature selected both over the entire length and over the entire cross-section of the reactor. In order to dissipate the heat of the reaction which is accompanied by a positive heat effect, cold hydrogen can be introduced through gas-inlet openings distributed over the length and circumference of the reactor, in dependence upon the temperature of the corresponding reactor zones, in such a way that the quantity of heat required to heat it to the reaction temperature is just supplied by the heat of reaction. At the same time, the quantity of starting material added to the hydrogen circuit is adapted in such a way that, during the reaction, it consumes at least the hydrogen required in this way for keeping the reactor at constant temperature. Extra hydrogen required for the reaction is intduced into the hydrogen circuit before the starting material is added. In addition, the reactor can be additionally cooled in conventional manner by dissipating the heat of reaction through the reaction wall by external cooling, for example with air or cooling liquids, or if necessary may even be insulated against heat loss or if necessary heated by external heating. External heating can also be used for reducing the catalyst, as described above, and for starting up the reactor.

The "product stream" leaving the reactor which, in addition to the excess hydrogen and the reaction products, may contain inert constituents such as nitrogen or methane, which may have been present in the hydrogen used, is used in the heat exchanger for heating the stream of hydrogen laden with starting material, as described above, and at the same time is cooled to a considerable extent. In a following condenser, it is further cooled to a temperature in the range of from about 20° to about 50° C. The liquid reaction products are then separated and collected in a suitably designed separator. The reaction products are taken out of the circuit through a level-controlled outlet, so that there is no unnecessary loss of pressure in the circuit. The hydrogen circuit is then brought back to such a pressure, for example by means of a recirculating pump, that the recycle stream has the reaction pressure selected at the reactor inlet, taking into account the freed hydrogen and starting material introduced under pressure and the heat effect.

Depending on its origin, the hydrogen can contain inert constituents such as nitrogen or methane which accumulate with time in the hydrogen circuit. To remove them, a component stream is removed from the hydrogen circuit following removal of the reaction products and replaced by an equivalent component stream of fresh hydrogen which is either free from or low in inert constituents. This can be done intermittently or even continuously. With continuous replacement, this fresh hydrogen is with advantage introduced in conjunction with the hydrogen required for the reaction, which is added before the starting material, i.e. in one stream at one point.

The d,l-menthol is advantageously separated off, for example by distillation, from the reaction products removed from the circuit and the remaining reaction products returned as starting material to the reaction following the addition of, for example, from 30 to 80% by weight of thymol. The quantity of starting materials added to the recycle stream thus obtained is with particular advantage substantially commensurate with that in which d,l-menthol is removed. The hydrogen which is not consumed in the reaction is also recycled, as described above, the fresh hydrogen being advantageously added to the hydrogen circuit before the starting material in correspondingly adapted distribution in such a way that the selected hydrogen pressure is maintained in the reactor.

Where figures separated by an oblique line are quoted as analytical data in the following Examples, they represent the results of independent double determinations.

Where thymol contents determined by UV-analysis are quoted in the following Examples, they represent the content of thymol and other aromatic compounds, expressed as thymol.

The "balance yield" quoted in the Examples is defined as follows:

Weighed quantity of reaction products in percent of the sum of the quantity of starting material used and the quantity of hydrogen theoretically required for its hydrogenation over the same period in each case. In the normal case, it should amount to around 100% within the limits of error of the methods used for determination; otherwise the starting material or the reaction products are lost through leaks in the system or with the component stream of hydrogen removed to reduce the inert-constituent content of the recycle stream.

EXAMPLES

A tube 90 mm in internal diameter and 1800 mm long filled with 12 liters of catalyst was used in the following Examples. 30 Nm$^3$ per hour of hydrogen and 2.4 liters per hour of starting material were passed downwards through the tube in the gas- or trickle-phase at a temperature of from 205° C and under a pressure of 280 bars, followed after condensation by continuous separation in the liquid phase from the excess hydrogen gas stream.

The reaction product was analysed by conventional methods (for example UV-spectrography, gas chromatography).

EXAMPLE I

The catalyst used in the following Examples (1 to 12) was prepared as follows: To begin with, 32.5 kg of an aqueous manganese nitrate ($Mn(NO_3)_2$) solution with a manganese content of 469 per kg of solution and a pH-value of about 1, containing a small quantity of hydrogen peroxide to prevent the formation of manganese dioxide, were adjusted to pH 4.5 by the addition with stirring of a 24% by weight aqueous potassium carbonate solution so that iron impurities were precipitated and the precipitate was filtered off in the form of hydroxides. The same procedure was repeated using 112 kg of an aqueous cobalt chloride ($CoCl_3$) solution with a cobalt content of 45 g of Co per kg and a pH-value of about 3.5, again to precipitate iron. The two solutions, freed from iron hydroxide by filtration, were then combined, admixed with a solution of 0.1 kg of copper sulphate, containing water of crystallisation ($Cu\ SO_4$–$5H_2O$) in 6 kg of water and then adjusted to a distinctly alkaline pH by the addition with stirring of more potassium carbonate solution in the concentration specified above, which required approximately 100 kg of calcium carbonate solution. The precipitate formed was separated off from the mother liquor by filtration and washed free from alkali with deionised water. It was then dried at 105° C and decarbonised at 300° C by the elimination of $CO_2$. After size reduction, it was moulded into tablets 5 mm thick and 5 mm in diameter following the addition of from 1 to 2% of graphite as lubricant. One run produced about 10 kg of catalyst with a powder density of about 1.25; a cobalt content of 49.7% by weight, a manganese content of 14.8% by weight (= 22.9% by weight of the total quantities of oxidic cobalt and oxidic manganese) and a copper content of 0.2% by weight.

12 Liters of the catalyst thus prepared were introduced into the reaction tube and reduced by initially passing nitrogen through the reaction tube at 100° C/normal pressure and then replacing the nitrogen, while slowly increasing the temperature, with a nitrogen/hydrogen mixture with a continuously increasing hydrogen content until finally at 300° C the nitrogen-hydrogen mixture had been completely replaced by hydrogen. These conditions were maintained for several hours until a sample of the catalyst, when analysed by X-ray photography in the absence of air, did not show any reflexes attributable to the presence of crystalline cobalt or crystalline manganese compounds.

The temperature was then reduced to 205° C, the hydrogen pressure increased to 280 bars and the starting material immediately introduced at a rate of 2400 ml per hour.

EXAMPLE 1

A mixture of 20% by weight of d-neomenthol ($\alpha_D^{18}$ = 18.5°), consisting of 94.6% of d-neomenthol, 4.9% of d,l-menthol, 0.4% of menthone and 0.1% of hydrocarbons, and 80% of thymol (DAB VII), with a solidification point of 49.4° C and a purity of more than 99%, was used as a starting material in accordance with the general conditions described above.

From this starting material, consisting of:
80.00% of thymol;
18.90% of d-neomenthol;
1.00% of d,l-menthol;
0.08% of menthone; and
0.02% of hydrocarbons
a reaction product of the following composition was obtained
59.7% of d,l-menthol;
29.3% of d,l-neomenthol;
10.6% of d,l-isomenthol;
0.38% of menthenone, menthone and neoisomenthol;
0.04% of hydrocarbons; and
0.01% of residue (higher-boiling).

This corresponds to a ratio of 59.9% of d,l-menthol, 29.45% of d,l-neomenthol, 10.65% of d,l-isomenthol; the reaction product was optically inactive; a value of $\alpha_D^{20}$ = −0.1° had not been exceeded even after 2814 hours of operation. The reaction product had an OH-number of 346/354; thymol could not be detected by UV-analysis (<10 ppm). The balance yield amounted to 99.4% of the theoretical yield.

EXAMPLE 2

A mixture of 80% by weight of thymol and 20% by weight of d-menthol ($\alpha_D^{18}$ = +50°) was used as starting material in accordance with the general conditions described above. A reaction product of the following composition was obtained:
59.6% by weight of d,l-menthol;
29.3% by weight of d,l-neomenthol;
10.6% by weight of d,l-isomenthol;
0.37% by weight of menthenone, menthone and neoisomenthol;
0.05% by weight of hydrocarbons.

This corresponds to a ratio of 59.8% of d,l-menthol, 29.55% of d,l-neomenthol, 10.65% of d,l-isomenthol; the reaction product was optically inactive. It had an OH-number of 348 – 354; thymol could not be detected by UV-analysis.

The balance yield amounted to 99.5% of the theoretical yield.

EXAMPLE 3

A mixture of 80% by weight of thymol and 20% by weight of l-menthol was used as starting material in accordance with the general conditions described above.

The composition of the reaction product obtained was the same as in Example 1. The reaction product was optically inactive and had an OH-number of 347/353; thymol could not be detected by UV-analysis.

The balance yield amounted to 99.8% of the theoretical yield.

EXAMPLES 4 and 5

These Examples were carried out in accordance with the general conditions described above, using as starting material the mixture described in Example 1 of 20% by weight of d-neomenthol and 80% by weight of thymol (DAB 7) to which 10 and 20% by weight, respectively, of a menthone of the composition:
99.8% by weight of menthone;
0.1% by weight of menthenone; and
0.1% by weight of hydrocarbons had been added.

EXAMPLE 4

The starting material had the following composition according to analysis:
72.70% of thymol;
17.20% of d-neomenthol;
0.90% of d,l-menthol;
9.15% of menthone;
0.01% of menthenone; and
0.03% of hydrocarbons.

A reaction product of the following composition was obtained:
59.5% of d,l-menthol;
29.4% of d,l-neomenthol;
10.6% of d,l-isomenthol;
0.4% of menthone and menthenone; and
0.07% of hydrocarbons.

The reaction product was optically inactive and had an OH-number of 342/352; thymol could not be detected by UV-analysis.

The balance yield amounted to 99.7% of the theoretical yield.

EXAMPLE 5

By adding 20% by weight of menthone of the composition specified in Example 4 to the starting material used in Example 1, and using the resulting starting material under the general conditions described above, a reaction product of the following composition, according to analysis, was obtained:
59.6% of d,l-menthol;
29.3% of d,l-neomenthol;
10.6% of d,l-isomenthol;
0.45% of menthone and menthenone; and
0.05% of hydrocarbons.

It did not have any optical rotation; its OH-number amounted to 342/350; the thymol content according to UV-analysis amounted to less than 0.02% by weight.

The balance yield amounted to 99.6% of the theoretical yield.

EXAMPLE 6

The mixture described in Example 1 was used as the starting material in accordance with the general conditions described above, following the addition of 10% by weight of a 99.7% by weight menthenone (rest menthone) which according to analysis had the following composition:
66.05% of thymol;
15.70% of d-neomenthol;
0.85% of d,l-menthol;
8.40% of menthone;
9.00% of piperitone; and
0.03% of hydrocarbons.

A reaction product of the following composition, according to analysis, was obtained.
- 59.6% of d,l-menthol;
- 29.1% of d,l-neomenthol;
- 10.8% of d,l-isomenthol;
- 0.42% of menthone and menthenone; and
- 0.05% of hydrocarbons.

It was optically inactive and had an OH-number of 342/350; according to UV-analysis, the reaction product had a thymol content of less than 0.02% by weight.

The balance yield amounted to 99.8% of the theoretical yield.

EXAMPLE 7

A mixture of 10% by weight of d-neomenthol ($\alpha_D^{18}$ = 18.5°) of the composition described in Example 1, 10% by weight of d,l-neomenthol (100%) and 80% by weight of thymol (DAB 7), was used as starting material in accordance with the general conditions described above.

A reaction product of the following composition was obtained:
- 59.7% of d,l-menthol;
- 29.4% of d,l-neomenthol;
- 10.5% of d,l-isomenthol;
- 0.4% of menthones; and
- 0.04% of hydrocarbons.

The reaction product had an OH-number of 348/352 and a thymol content according to UV-analysis of less than 0.01%. The reaction product was optically inactive.

The balance yield amounted to 99.8 % of the theoretical yield.

EXAMPLE 8

A mixture of 10% by weight of d-neomenthol of the composition described in Example 1, 10% by weight of d,l-isomenthol (100%) and 80% of thymol (DAB 7), was used as starting material in accordance with the general conditions described above.

A reaction product of the following composition was obtained:
- 59.8% of d,l-menthol,
- 29.2% of d,l-neomenthol;
- 10.6% of d,l-isomenthol;
- 0.4% of menthones, and
- 0.04% of hydrocarbons.

The reaction product had a rotation of $\alpha_D^{20} \leq 0.1°$ and an OH-number of 340/354; according to UV-analysis, it had a thymol content of less than 0.01%.

The balance yield amounted to 99.7% of the theoretical yield.

EXAMPLE 9

A reaction product of the following composition was obtained in accordance with the general conditions described above from a starting material consisting of 75% by weight of d,l-neomenthol and 25% by weight of d,l-isomenthol:
- 59.2% of d,l-menthol;
- 26.9% of d,l-neomenthol;
- 10.8% of d,l-isomenthol;
- 0.4% of menthone; amd
- 0.03% of hydrocarbons.

It was optically inactive and had an OH-number of 345 to 350.

The balance yield amounted to 99.7% of the theoretical yield.

EXAMPLE 10

A mixture of the following composition was used as starting material in accordance with the general conditions described above:
- 60.0% of thymol;
- 30.0% of d,l-neomenthol;
- 8.0% of d,l-isomenthol;
- 1.6% of d,l-menthol;
- 0.04% of menthone, piperitone; and
- 0.02% of hydrocarbons.

A reaction product of the following composition was obtained:
- 59.7% of d,l-menthol;
- 29.2% of d,l-neomenthol;
- 10.7% of d,l-isomenthol;
- 0.04% of menthone; and
- 0.04of hydrocarbons.

The reaction product was optically inactive and had an OH-number of 345/353, even after 1874 hours of operation; thymol could not be detected UV-analysis.

The balance yield amounted to 99.6% of the theoretical yield.

EXAMPLE 11

Mixtures of 50 to 70% by weight of thymol with 50 to 30% by weight of d-neomenthol or d-menthol were used as starting material in accordance with the general conditions described above. In Table I below, column 1 gives the composition of the starting material, column 2 the balance yield of d,l-menthol in percent of the theoretical, whilst the other columns give the contents in the reaction product of d,l-neomenthol, d,l-isomenthol, menthone and other ketones, also hydrocarbons, the OH-number, the optical rotation and the thymol content, calculated from the UV-absorption.

Table I

| Starting material | Balance yield % of theoretical | d,l-menthol % by weight | d,l-neo-menthol % by weight | d,l-iso-menthol % by weight | menthone and others % by weight | hydrocarbons % by weight | OH-number | thymol UV-analysis | optical rotation |
|---|---|---|---|---|---|---|---|---|---|
| 70 % thymol 30 % d-neo-menthol | 99.5 % | 59.6 | 29.3 | 10.7 | 0.4 | 0.04 | 348/348 | 18 ppm | <0.1° |
| 60 % thymol 40 % d-neo-menthol | 99.6% | 59.7 | 29.3 | 10.6 | 0.4 | 0.03 | 346/348 | 11 ppm | < 0.1° |
| 50 % thymol 50 % d-neo-menthol | 99.8 % | 59.5 | 29.6 | 10.6 | 0.4 | 0.03 | 348/353 | 12 ppm | < 0.1° |
| 70 % thymol 30 % d-menthol | 99.5 % | 59.4 | 29.7 | 10.8 | 0.5 | 0.04 | 346/354 | 8 ppm | < 0.1° |
| 60 % thymol 40 % d-menthol | 99.9 % | 59.8 | 29.3 | 10.9 | 0.3 | 0.06 | 347/348 | 12 ppm | < 0.1° |
| 50 % thymol | 99.8 % | 59.6 | 29.4 | 10.8 | 0.4 | 0.04 | 350/ | 2 ppm | < 0.1° |

Table I-continued

| Starting material | Balance yield % of theoretical | d,1-menthol % by weight | d,1-neo-menthol % by weight | d,1-iso-menthol % by weight | menthone and others % by weight | hydrocarbons % by weight | OH-number | thymol UV-analysis | optical rotation |
|---|---|---|---|---|---|---|---|---|---|
| 50 % 1-menthol | | | | | | | 353 | | |

EXAMPLE 12

Mixtures of thymol and/or optically active or inactive stereoisomers of menthol whose exact composition (purity) was not analyzed in detail, were used as starting material in accordance with the general conditions described above. In Table II below, column 1 gives the composition of the starting material, column 2 the balance yield in % of the theoretical whilst the remaining columns give the composition and properties of the reaction product, as in Table I.

tioned concentration. The precipitate formed was separated from the mother liquor by filtration and washed free from alkali with deionised water. It was then dried at 105° C and decarbonised at 300° C. After size reduction, it was moulded into 5 mm thick, 5 mm diameter tablets following the addition of 1 to 2% of graphite as lubricant. The resulting catalyst then had the manganese content specified in Table III below, based on the total quantities of cobalt and manganese.

12 Liters of the catalyst thus prepared were then introduced into the reaction furnace and reduced as Table II

| Starting Material | Balance yield % of theoretical | d,1-menthol % by weight | d,1-neo-menthol % by weight | d,1-iso-menthol % by weight | menthone and others % by weight | hydro-carbons % by weight | OH-number | thymol UV-analysis | optical rotation |
|---|---|---|---|---|---|---|---|---|---|
| 30 % thymol 70 % d-menthol | 99.7 | 59.8 | 29.3 | 10.8 | 0.3 | 0.05 | 352/353 | 9 ppm | < 0.1° |
| 40 % athymol 60 %, d,1-neo-menthol | 99.8 | 59.5 | 29.7 | 10.7 | 0.5 | 0.04 | 348/a351 | 4 ppm | — |
| 20 % thymol 30 % 1-menthol 50 % d,1-neo-menthol | 99.6 | 59.4 | 29.7 | 10.9 | 0.3 | 0.04 | 346/350 | — | < 0.1° |
| 40 % d,1-iso-menthol | 99.9 | 59.6 | 29.2 | 10.9 | 0.4 | 0.03 | 347/350 | 7 ppm | — |
| 20 % thymol 20 % d-neomenthol 20 % d,1-iso-menthol | 100.0 | 59.7 | 29.4 | 10.8 | 0.4 | 0.02 | 347/351 | 6 ppm | < 0.1° |
| 20 % d-neomenthol 20 % d,1-iso-menthol | 99.6 | 59.5 | 29.8 | 10.6 | 04 | 0.04 | 348/353 | 11 ppm | < 0.1° |

EXAMPLE II

The catalyst used in the following Examples (13 to 16) was prepared as follows:

As in Example I, the quantity specified in Table III below of aqueous manganese nitrate solution having a manganese content of 46 g per kg of solution and a pH-value of about 1, containing a small quantity of hydrogen peroxide to prevent manganese dioxide formation, was adjusted to pH 4.5 by the addition with stirring of a 24% by weight potassium carbonate solution, and hence the iron impurities were precipitated and filtered off in the form of hydroxide. The same procedure was then repeated with 112 kg of an aqueous cobalt chloride solution with a Co-content of 45 g per kg of solution and a pH-value of about 3.5, again to precipitate iron. The two solutions freed from iron hydroxide by filtration were combined, admixed with the quantity, specified in Table III below, of a solution of 0.1 kg of copper sulphate, containing water of crystallisation. Co(SO$_4$)-5H$_2$O in 6 kg of water and a distinctly alkaline pH adjusted by the addition with stirring of more potassium carbonate solution in the aforementioned concentration.

described in Example I until a sample of the catalyst, when analysed by X-ray photography in the absence of air, did not show any reflexes attributable to the presence of crystalline cobalt or crystalline manganese compounds.

The temperature was then reduced to 205° C, the hydrogen pressure increased to 280 bars and the starting material immediatedly introduced at a rate of 2400 ml per hour, in accordance with the general conditions described above.

EXAMPLES 13 to 16

In Examples 13 to 16 the same starting material is used as in Example 1.

Table III below shows the Example No., the quantity of aqueous manganese nitrate solution and copper sulphate solution used to produce the catalyst, the manganese content of the catalyst based on the total quantity of cobalt and manganese and the composition and analysis of the reaction product, in the same way as Tables I and II.

The corresponding values of Example 1 are also shown in the Table for comparison.

Table III

| Example No. | Mn(NO$_3$)$_2$ solution kg | CuSO$_4$ solution kg | Catalyst Mn-content % | d,1-menthol % by weight | d,1-neo-menthol % by weight | d,1-iso-menthol % by weight | menthone and others % by weight | hydro-carbons | UV-analysis | optical rotation | OH-number |
|---|---|---|---|---|---|---|---|---|---|---|---|
| 13 | 12.57 | 0.1 | 10.15 | 57.1 | 27.8 | 9.4 | 1.5 | 4.3 | 400 ppm | −0.4° | 318/327 |
| 13a | after 32 days of operation | | | 57.6 | 27.5 | 9.2 | 1.7 | 4.5 | 450 ppm | −0.8° | 312/317 |

Table III-continued

| Example No. | Mn(NO₃)₂- solution kg | CuSO₄- solution kg | Catalyst Mn-content % | Reaction product d,l-menthol % by weight | d,l-neo-menthol % by weight | d,l-iso-menthol % by weight | menthone and others % by weight | hydro-carbons | UV-analysis | optical rotation | OH-number |
|---|---|---|---|---|---|---|---|---|---|---|---|
| 147 | 24.5 | 0.1 | 18.05 | 58.2 | 28.1 | 10.2 | 1.3 | 2.2 | 300 ppm | −0.3° | 327/342 |
| Original catalyst for comparison | | | | | | | | | | | |
| 1 | 32.5 | 0.1 | 22.9 | 59.7 | 29.3 | 10.6 | 0.38 | 0.04 | 10 ppm | −0.1° | 346/364 |
| 15 | 45.0 | 0.1 | 29.2 | 58.3 | 27.2 | 10.3 | 1.1 | 2.4 | 400 ppm | −0.3° | 329/341 |
| 16 | 67.5 | 0.1 | 38.2 | 56.3 | 27.5 | 11.4 | 1.1 | 4.6 | 480 ppm | −0.3° | 319/322 |
| 16 | after 18 days of operation | | | 56.6 | 27.8 | 10.4 | 0.9 | 4.3 | 500 ppm | −0.6° | 318/323 |

EXAMPLE 17

This Example demonstrates the use of a catalyst that is not activated with copper.

A non-copper-activated catalyst, having a manganese content was identical with that of the catalyst prepared in accordance with Example I, was prepared in accordance with the procedure of Example I, but without addition of the copper sulphate solution. 12 liters of this catalyst were introduced into the reaction tube and reduced as described in Example 1. The temperature was then reduced to 205° C, the hydrogen pressure increased to 280 bars and the starting material immediately introduced at a rate of 2400 ml per hour. Hydrogen was introduced at the rate of 30 Nm³ per hour.

The same mixture as in Example 1 was used as the starting material in accordance with the general conditions described above. A reaction product of the following composition was obtained:

59.7% by weight of d,l-menthol;
29.3% by weight of d,l-neomenthol;
10.6% by weight of d,l-isomenthol;
0.38% by weight of menthenone, menthone and neoisomenthol;
0.04% by weight of hydrocarbon; and
0.02% by weight of residue (higher-boiling, cf. Example 1).

The reaction product was optically inactive and had an OH-number of 347/354; thymol could not be detected by UV-analysis.

Comparison with Example 1 shows that the composition of the reaction product is substantially the same except for the larger residue.

EXAMPLE 18 (comparison Example)

This Example demonstrates the use of a cobalt catalyst activated solely with manganese.

A catalyst was prepared in the same way as described in Example I, except that only 1.4 kg as opposed to 32.5 kg of aqueous manganese nitrate solution were used. The necessary quantity of potassium carbonate solution was also correspondingly smaller. The catalyst thus prepared contained 1.21% by weight of manganese, based on the total quantity of cobalt and manganese. 12 Liters of the resulting catalyst were subsequently introduced into the reaction furnace and reduced as described in Example I until a sample of the catalyst, when analysed by X-ray photography in the absence of air, did not show any reflexes attributable to the presence of crystalline cobalt or crystalline manganese compounds.

The temperature was then reduced to 205° C, the hydrogen pressure increased to 280 bars and the starting material immediately introduced at a rate of 2400 ml per hour in accordance with the general conditions described above.

The starting material used in Example 1 was used as the starting material; the reaction product had the following composition:

57.0% by weight of d,l-menthol;
27.5% by weight of d,l-neomenthol;
9.7% by weight of menthenone, menthone and neoisomenthol; and
4.2% by weight of hydrocarbons.

The reaction product had an OH-number of 319/326 and a thymol content of 450 ppm (UV-analysis); $\alpha_D^{20}$ = −0.6°.

Catalysts according to the prior art (U.S. Patent Specification Nos. 2,843,636 and 2,871,272).

Comparison Example a)

A copper chromite catalyst of the following composition:

58.9% of CuO;
38.1% of $Cr_2O_3$; and
3.0% of $H_2O$ was moulded into 5 mm diameter, 5 mm thick tablets following the addition of 1 to 2% by weight of graphite as lubricant. These tablets were broken up and remoulded into tablets 5 mm in diameter and 5 mm thick.

12 Liters of the resulting catalyst were introduced into the reaction tube described above and reduced by initially passing nitrogen through the reaction tube at 100° C/normal pressure and then replacing the nitrogen, while slowly increasing the temperature, by a nitrogen-hydrogen mixture with a continuously increasing hydrogen content until finally at 350° C the nitrogen-hydrogen mixture had been completely replaced by hydrogen. This temperature was maintained for several hours.

The temperature was then reduced to 200° C, the hydrogen pressure increased to 280 bars and the starting material described in Example 1 introduced at a rate of 2400 ml/hour.

The reaction product obtained had the following composition:

56.2% of d,l-menthal,
27.6% of d,l-neomenthol,
10.4% of d,l-isomenthal,
1.7% of menthenone, menthone and neoisomenthol; and
4.1% of hydrocarbons which corresponds to a ratio of 59.7% of d,l-menthol, 29.2%, 11.1% of d,l-isomenthol.

After 456 hours, of operation, the optical rotation amounted to $\alpha_D^{20}$ = −0.2°. The reaction product obtained had an OH-number of 319/334 (calculated 326). According to UV-spectral analysis, the reaction product had an unreacted thymol content of 0.05 - 0.1%.

Comparison Example b)

Commercial-grade water-moist Raney nickel was moulded in an inert gas atmosphere (nitrogen) into 5 mm thick, 5 mm diameter tablets. The resulting tablets were size-reduced under water and remoulded water-moist into 5 mm thick, 5 mm diameter tablets following the addition of 1 to 2% by weight of graphite as lubricant.

12 Liters of the catalyst thus obtained were introduced under water into the reaction furnace described above. The catalyst was then dried by initially passing nitrogen through the reaction tube at 100° C/normal pressure and then replacing the nitrogen, while slowly increasing the temperature, by a mixture of nitrogen and hydrogen with a continuously increasing hydrogen content until finally at 200° C the nitrogen-hydrogen mixture had been completely replaced by hydrogen.

The temperature was then increased to 210° C, the hydrogen pressure to 280 bars and the starting material described in Example 1 was introduced at a rate of 2400 ml/hour.

A reaction product of the following composition was obtained:
- 56.1 of d,l-menthol;
- 27.3% of d,l-neomenthol;
- 10.4% of d,l-isomenthol;
- 1.4% of menthenone, menthone, neoisomenthol; and
- 4.8% of hydrocarbons corresponding to a specific ratio of
- 59.8% of d,l-menthol;
- 29.1% of d,l-neomenthol; and
- 11.1% of d,l-isomenthol.

After 287 hours of operation, the optical activity $a_D^{20} = -0.3°$; the reaction product had an OH-number of 314 to 325. According to UV-spectral analysis, it had an unreacted thymol content of less than 0.05%.

The balance yield amounted to 98.5% of the theoretical yield.

What is claimed is:

1. In a process for production of d,l-menthol by contacting a starting material which is a compound having the carbon skeleton of menthol and which is convertible to d,l-menthol by catalytic hydrogenation, and having at least one double bond and being substituted in the 4-position by oxygen, with hydrogen in the presence of a catalyst for hydrogenation of said starting material, in a contacting zone, at a temperature, pressure, and residence time sufficient for the hydrogenation to form said d,l-menthol, the improvement which comprises employing as said catalyst a cobalt-manganese catalyst containing 20 to 25% by weight of manganese, based on the total quantity of cobalt and manganese, and activated with up to 1% by weight of copper based on the total weight of the catalyst, and operating the process continuously by continuously introducing said starting material and hydrogen into the contacting zone and continuously withdrawing the d,l-menthol from the contacting zone.

2. A process according to claim 1, the temperature being 170° to 220° C, the pressure being at least 25 bars, and the amount of hydrogen being at least 10 times the amount required to fully hydrogenate X moles of benzene, wherein X is the moles of starting material.

3. A process according to claim 1, the catalyst being the product of precipitating the hydroxides or carbonates of cobalt and manganese, calcining the precipitate to product oxide of the cobalt and manganese, and reducing the oxide with hydrogen, the reduced catalyst when analyzed by X-ray photography in the absence of air showing no reflexes attributable to the presence of crystalline cobalt or crystalline manganese compounds.

4. A process according to claim 1, the starting material being of the formula:

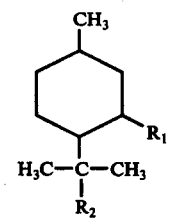

wherein:
- $R_1$ is oxygen or hydroxy
- $R_2$ is hydrogen or nothing and when
- $R_2$ is nothing, the isopropylidene group is bonded to the ring by a double bond, and there is at least one double bond in the compound.

5. A process according to claim 1, wherein the catalyst is activated with from 0.05 to 0.5% by weight of copper based on the total weight of the catalyst.

6. A process according to claim 1, wherein the hydrogenation is carried out at a temperature in the range of from 180° C to 210° C.

7. A process according to claim 1, wherein the hydrogenation is carried out under a pressure of higher than 100 bars.

8. Process according to claim 7, wherein hydrogenation is carried out under a pressure of more than 200 bars.

9. A process according to claim 6, wherein the hydrogenation is carried out under a pressure of higher than 100 bars.

10. A process according to claim 9 wherein the catalyst is used immediately after its reduction.

11. Process of claim 1, wherein the starting material is at least one of thymol, menthone, 1-p-menthan-3-one, menthenone, piperitone, pulegone d-menthol, l-menthol, d-neomenthol, l-neomenthol, d-isomenthol, l-isomenthol d,l-neomenthol, d,l-isomenthol.

12. Process of claim 2, wherein the starting material is at least one of thymol, menthone, 1-p-menthan-3-one, menthenone, piperitone, pulegone d-menthol, l-menthol, d-neomenthol, l-neomenthol, d-isomenthol, l-isomenthol, d,l-neomenthol, d-l-isomenthol.

13. Process of claim 1, wherein the starting material is thymol.

14. Process of claim 2, wherein the starting material is thymol.

* * * * *

UNITED STATES PATENT AND TRADEMARK OFFICE
CERTIFICATE OF CORRECTION

PATENT NO. : 4,058,571
DATED : November 15, 1977
INVENTOR(S) : Wolfgang Biedermann It is certified that error appears in the above-identified patent and that said Letters Patent are hereby corrected as shown below:

Col. 3, line 63, change "methods cf." to -- methods (cf. --.

Col. 5, line 27, change "freed" to -- fresh --.

Col. 10, line 11, change "amd" to -- and --.

Col. 10, line 33, change "menthone" to -- menthones --.

Col. 10, line 34, change "0.04of" to -- 0.04% of --.

Col. 11, Table II, 1st col., line 3, change "athymol" to -- thymol --.

Col. 12, Table II, 8th col., line 4, change "a351" to -- 351 --.

Col. 11, Table II, 1st col., line 7, change "30%" to -- 80% --.

Col. 11, Table II, 1st col., line 8, change "50%" to -- 60% --.

Col. 11, Table II, 1st col., 4th from last line, change "20%" to -- 60% --.

Col. 11, Table II, 1st col., next to last line, change "20%" to -- 70% --.

Col. 11, Table II, 1st col., last line, change "20%" to -- 30% --.

UNITED STATES PATENT AND TRADEMARK OFFICE
CERTIFICATE OF CORRECTION

PATENT NO. : 4,058,571
DATED : November 15, 1977
INVENTOR(S) : Wolfgang Biedermann It is certified that error appears in the above-identified patent and that said Letters Patent are hereby corrected as shown below:

Col. 11, Table II, col. 6, last line, change "04" to -- 0.4 --.

Col. 11, line 50, change "hydroxide" to -- hydroxides --.

Col. 12, Table III, Title of 10th col., insert "thymol" above "UV-analysis".

Col. 11, Table III, col. 2, line 1, change "12.57" to -- 12.5 --.

Col. 14, Table III, col. 10, Title, insert "thymol" above -- "UV-analysis".

Col. 13, Table III, col. 1, change "147" to -- 14 --.

Col. 14, line 58, change "isomenthal" to -- isomenthol --.

Col. 16, line 6, change "product" to -- produce --.

Signed and Sealed this

Twenty-third Day of May 1978

[SEAL]

Attest:

RUTH C. MASON
Attesting Officer

LUTRELLE F. PARKER
Acting Commissioner of Patents and Trademarks